(12) United States Patent
Krieb et al.

(10) Patent No.: US 7,718,373 B2
(45) Date of Patent: May 18, 2010

(54) CANOLA EVENT PV-BNGT04(RT73) AND COMPOSITIONS AND METHODS FOR DETECTION THEREOF

(75) Inventors: Rachel Krieb, Wood River, IL (US); Qingyi Zeng, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 154 days.

(21) Appl. No.: 11/980,313

(22) Filed: Oct. 30, 2007

(65) Prior Publication Data

US 2008/0070260 A1   Mar. 20, 2008

Related U.S. Application Data

(62) Division of application No. 10/415,305, filed as application No. PCT/US01/48583 on Oct. 22, 2001, now Pat. No. 7,306,909.

(60) Provisional application No. 60/244,346, filed on Oct. 30, 2000.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/23.2; 536/23.6; 536/24.33

(58) Field of Classification Search .............. 435/6, 435/91.2; 536/23.2, 23.6, 24.33
See application file for complete search history.

(56) References Cited

U.S. PATENT DOCUMENTS

| 5,633,435 | A | 5/1997 | Barry et al. | |
| 5,962,768 | A | 10/1999 | Cornelissen et al. | |
| 6,531,649 | B1 * | 3/2003 | Mannerloef et al. | 800/300 |
| 2008/0070260 | A1 * | 3/2008 | Krieb et al. | 435/6 |

FOREIGN PATENT DOCUMENTS

| EP | 0 218 571 A2 | 4/1987 |
| WO | WO 02/44407 A2 | 6/2002 |

OTHER PUBLICATIONS

The attached nucleic acid sequence search report for SEQ ID No. 7.*
Windels, Pieter, et al., Characterisation of the 3' NOS junction of Roundup Ready soy, *Mededelingen Faculteit Landbouwkundige en Toegepaste Biologische* 65(3B):463-465 (2000).
Zimmermann, Andreas, et al., Event specific transgene detection in BT11 corn by quantitative PCR at the integration site, *Lebensmittle-Wissenschaft & Technologies* 33(3):210-216 (2000).
Windels, Pieter, et al., Development of a line specific GMO detection method: a case study, *Mededelingen van de Faculteit Landbouwwetenschappen Universiteit Gent*, Gent, BE 64(5b):459-462 (1999) (labeled XP-001032975).
Kumar, S., Populus tremula transgenic line Braunall:35S-rolC#2 junction genomic sequence/left T-DNAA border, GenBank accession No. AJ296083 (abstract), Oct. 4, 2000.
Spertini, Diego, et al., Screening of transgenic plants by amplification of unknown genomic DNA flanking T-DNA, *BioTechniques* 27(2):308-314 (1999) (labeled XP-001145764).
Terry, Catherine F., et al., Event-specific detection of Roundup Ready Soya using two different real time PCR detection chemistries, *European Food Research and Technology* 213(6):425-431 (2001) [labeled XP-001097295].
Wells, B.H., Development of glyphosate tolerant crops into the market, *Chemical Abstracts* 124(8):494, abstract No. 79375m (1996) [labeled XP-002013733].
Windels, Pieter, et al., Characterisation of the Roundup Ready soybean insert, *European Food Research and Technology* 213(2):107-112 (2001) [labeled XP-008072737].
Canadian Food Inspection Agency, Plant Health and Production Division, Plant Biosafety Office, "Decision Document DD95-02: Determination of Environmental Safety of Monsanto Canada Inc.'s Roundup® Herbicide-Tolerant *Brassica napus* Canola Line GT73," http://www.inspection.gc.ca/english/plaveg/bio/dd/dd9502e.shtml, Mar. 19, 2005.
Office of Food Biotechnology, Food Directorate, Health Protection Branch, Health Canada, "Novel Food Information—Good Biotechnology Glyphosate Tolerant Canola, GT73," FD/OFB-094-325-A, Oct. 1999.

* cited by examiner

*Primary Examiner*—Kenneth R. Horlick
*Assistant Examiner*—Joyce Tung
(74) *Attorney, Agent, or Firm*—Pamela J. Sisson; Howrey LLP

(57) ABSTRACT

The present invention provides assays for detecting the presence of the PV-BNGT04(RT73) canola event based on the DNA sequence of the recombinant construct inserted into the canola genome and of genomic sequences flanking the insertion site.

10 Claims, No Drawings

US 7,718,373 B2

CANOLA EVENT PV-BNGT04(RT73) AND COMPOSITIONS AND METHODS FOR DETECTION THEREOF

CROSS REFERENCES TO RELATED APPLICATIONS

This application is a divisional of application Ser. No. 10/415,305, filed Apr. 28, 2003, issued as U.S. Pat. No. 7,306,909, which is a §371 application of PCT/US2001/048583, filed Oct. 22, 2001, which claims benefit of priority from U.S. Provisional Patent Application No. 60/244,346, filed Oct. 30, 2000.

FIELD OF THE INVENTION

The present invention relates to the field of plant molecular biology, more specifically the invention relates to transgenic glyphosate tolerance in a plant. The invention more specifically relates to a glyphosate tolerant canola plant PV-BNGT04(RT73) and to assays for detecting the presence of canola plant PV-BNGT04(RT73) DNA in a sample and compositions thereof.

BACKGROUND OF THE INVENTION

Canola is an important oil crop in many areas of the world. The methods of biotechnology have been applied to canola for improvement of the agronomic traits and the quality of the product. A method of introducing transgenes into *Brassica* species is demonstrated in U.S. Pat. No. 5,463,174. One such agronomic trait important in canola production is herbicide tolerance, in particular, tolerance to glyphosate herbicide. This trait has been introduced into canola plants and is a successful product now used in canola production. The expression of foreign genes in plants is known to be influenced by their chromosomal position, perhaps due to chromatin structure (e.g., heterochromatin) or the proximity of transcriptional regulation elements (e.g., enhancers) close to the integration site (Weising et al., Ann. Rev. Genet 22:421-477, 1988). For this reason, it is often necessary to screen a large number of events in order to identify an event characterized by optimal expression of a introduced gene of interest. For example, it has been observed in plants and in other organisms that there may be a wide variation in levels of expression of an introduced genes among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the premarket approval and labeling of foods derived from recombinant crop plants, for example. It is possible to detect the presence of a transgene by any well known nucleic acid detection method such as the polymerase chain reaction (PCR) or DNA hybridization using nucleic acid probes. These detection methods generally focus on frequently used genetic elements, such as promoters, terminators, marker genes, etc. As a result, such methods may not be useful for discriminating between different events, particularly those produced using the same DNA construct unless the sequence of chromosomal DNA adjacent to the inserted DNA ("flanking DNA") is known. An event-specific PCR assay is discussed, for example, by Windels et al. (Med. Fac. Landbouww, Univ. Gent 64/5b:459-462, 1999), who identified glyphosate tolerant soybean event 40-3-2 by PCR using a primer set spanning the junction between the insert and flanking DNA, specifically one primer that included sequence from the insert and a second primer that included sequence from flanking DNA.

This invention relates to the glyphosate herbicide tolerant canola (*Brassica napus*) plant PV-BNGT04(RT73) sold in the U.S.A. and other countries under the name Roundup Ready® canola and to the DNA molecules contained in these canola plants that are useful in detection methods for Roundup Ready® canola and progeny thereof.

SUMMARY OF THE INVENTION

According to one aspect of the invention, DNA sequences that comprise a polynucleotide of sufficient length of polynucleotides homologous to the transgene portion of the DNA sequence of SEQ ID NO:7 or complements thereof, and a similar length of polynucleotides homologous to the flanking canola DNA sequence of SEQ ID NO:7 or complements thereof, wherein the polynucleotide is useful as a DNA primer in DNA amplification methods or DNA hybridization methods.

According to another aspect of the invention, DNA sequences that comprise a sufficient length of polynucleotides of the transgene portion of the DNA sequence of SEQ ID NO:8 or complements thereof, and a similar length of polynucleotides homologous to the flanking canola DNA sequence of SEQ ID NO:8 or complements thereof, wherein the polynucleotide is useful as a DNA primer in DNA amplification methods or DNA hybridization methods.

According to an aspect of the invention, compositions and methods are provided for detecting the presence of the transgene/genomic insertion region from a canola plant designated PV-BNGT04(RT73) and plants and seeds thereof. DNA sequences are provided that comprise at least one transgene/genomic insertion region junction sequence of PV-BNGT04 (RT73) identified as SEQ ID NO:5 and SEQ ID NO:6, and complements thereof; wherein an insertion region junction sequence is a DNA polynucleotide sequence that spans the heterologous DNA inserted into the canola genome and the endogenous DNA of the canola genome at the insertion site and is diagnostic for the event.

According to another aspect of the invention, a DNA sequence that comprises the novel transgene/genomic insertion region, SEQ ID NO:7 is an aspect of this invention. Included are DNA sequences that comprise a sufficient length of polynucleotides of transgene insert sequence and a sufficient length of polynucleotides of canola genomic sequence from canola plant PV-BNGT04(RT73) of SEQ ID NO:7 that are useful as DNA primer polynucleotides for the production of an amplicon product diagnostic for canola plant PV-BNGT04(RT73). The DNA primer polynucleotides comprise a primer set. Therefore the invention also includes the primer set and the amplicons produced by primers sets wherein the DNA primer polynucleotides are homologous or complementary to SEQ ID NO:7.

According to another aspect of the invention, a DNA sequence that comprises the novel transgene/genomic insertion region, SEQ ID NO:8 is an aspect of this invention. Included are DNA sequences that comprise a sufficient length of polynucleotides of transgene insert sequence and a sufficient length of polynucleotides of canola genomic sequence from canola plant PV-BNGT04(RT73) of SEQ ID NO:8 that are useful as DNA primer polynucleotides for the production of an amplicon product diagnostic for canola plant PV-BNGT04(RT73). The DNA primer polynucleotides comprise a primer set. Therefore the invention also includes the primer set and the amplicons produced by primers sets wherein the DNA primer polynucleotides are homologous or complementary to SEQ ID NO:8.

According to another aspect of the invention, methods of detecting the presence of DNA corresponding to the canola event PV-BNGT04(RT73) event in a sample are provided. Such methods comprise: (a) contacting a DNA sample with a primer set, that when used in a nucleic acid amplification reaction with DNA from canola event PV-BNGT04(RT73) produces an amplicon that is diagnostic for canola event PV-BNGT04(RT73); (b) performing a nucleic acid amplification reaction, thereby producing the amplicon; and (c) detecting the amplicon.

According to another aspect of the invention, methods of detecting the presence of a DNA corresponding to the PV-BNGT04(RT73) event in a sample, such methods comprising: (a) contacting the sample comprising DNA with a probe that hybridizes under stringent hybridization conditions with DNA from canola event PV-BNGT04(RT73) and does not hybridize under the stringent hybridization conditions with a control canola plant (non-PV-BNGT04(RT73); and (b) subjecting the sample and probe to stringent hybridization conditions; and (c) detecting hybridization of the probe to the DNA.

According to another aspect of the invention, methods of producing a canola plant that tolerates application of glyphosate are provided that comprise the steps of: (a) sexually crossing a first parental canola line comprising the expression cassettes of the present invention, which confers tolerance to application of glyphosate, and a second parental canola line that lacks the glyphosate tolerance, thereby producing a plurality of progeny plants; and (b) selecting a progeny plant by the use of molecular markers SEQ ID NO:5 and SEQ ID NO:6, or complements thereof in a marker assisted breeding method. Such methods may optionally comprise the further step of back-crossing the progeny plant to the second parental canola line to producing a true-breeding canola plant that tolerates application of glyphosate.

According to another aspect of the invention, methods of determining the zygosity of progeny of a cross with PV-BNGT04(RT73) are provided. A method that comprises contacting a sample consisting of canola DNA with a primer set comprising SEQ ID NO: 13, SEQ ID NO: 14 and SEQ ID NO: 15, that when used in a nucleic-acid amplification reaction with genomic DNA from canola event PV-BNGT04 (RT73), produces a first amplicon that is diagnostic for canola event PV-BNGT04(RT73); and performing a nucleic acid amplification reaction, thereby producing the first amplicon; and detecting the first amplicon; and contacting the sample comprising canola DNA with said primer set, that when used in a nucleic-acid amplification reaction with genomic DNA from canola plants produces a second amplicon comprising the native canola genomic DNA homologous to the canola genomic region of a transgene insertion identified as canola event PV-BNGT04(RT73); and performing a nucleic acid amplification reaction, thereby producing the second amplicon; and detecting the second amplicon; and comparing the first and second amplicons in a sample, wherein the presence of both amplicons indicates the sample is heterozygous for the transgene insertion.

The foregoing and other aspects of the invention will become more apparent from the following detailed description and accompanying drawings.

DETAILED DESCRIPTION OF THE PREFERRED EMBODIMENTS

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular,* 5th edition, Springer-Verlag: New York, 1991; and Lewin, *Genes V,* Oxford University Press: New York, 1994. The nomenclature for DNA bases as set forth at 37 CFR §1.822 is used.

As used herein, the term "canola" means *Brassica napus* and includes all plant varieties that can be bred with canola, including wild *Brassica* species.

As used herein, the term "comprising" means "including but not limited to".

"Glyphosate" refers to N-phosphonomethylglycine and its salts, Glyphosate is the active ingredient of Roundup® herbicide (Monsanto Co.). Treatments with "glyphosate herbicide" refer to treatments with the Roundup®, Roundup Ultra® herbicide or any other herbicide formulation containing glyphosate. For the purposes of the present invention, the term "glyphosate" includes any herbicidally active form of N-phosphonomethylglycine (including any salt thereof) and other forms that result in the production of the glyphosate anion in plants. Treatments with "glyphosate" refer to treatments with the Roundup® or Roundup Ultra® herbicide formulation, unless otherwise stated. Plant transformation and regeneration in tissue culture use glyphosate or salts of glyphosate. Whole plant assays use formulated Roundup® or Roundup Ultra®. Additional formulations with herbicide activity that contain N-phosphonomethylglycine or any of its salts are herein included as a glyphosate herbicide.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA. A glyphosate tolerant canola plant can be breed by first sexually crossing a first parental canola plant consisting of a canola plant grown from the transgenic canola plant derived from transformation with the expression cassettes of the present invention that tolerates application of glyphosate herbicide, and a second parental canola plant that lacks the tolerance to glyphosate herbicide, thereby producing a plurality of first progeny plants; and then selecting a first progeny plant that is tolerant to application of glyphosate herbicide; and selfing the first progeny plant, thereby producing a plurality of second progeny plants; and then selecting from the second progeny plants a glyphosate herbicide tolerant plant. These steps can further include the back-crossing of the first glyphosate tolerant progeny plant or the second glyphosate tolerant progeny plant to the second parental canola plant or a third parental canola plant, thereby producing a canola plant that tolerates the application of glyphosate herbicide.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987).

Canola varieties containing genomic DNA from canola event PV-BNGT04(RT73) has been introduced into commercial germplasm and is commercially available in Roundup Ready® Canola varieties.

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from canola event PV-BNGT04(RT73) whether from a canola plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated polynucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 11 nucleotides or more in length, preferably 18 nucleotides or more, more preferably 24 nucleotides or more, and most preferably 30 nucleotides or more. Such probes and primers hybridize specifically to a target sequence under high stringency hybridization conditions. Preferably, probes and primers according to the present invention have complete sequence identity with the target sequence, although probes differing from the target sequence and that retain the ability to hybridize to target sequences under high stringency conditions may be designed by conventional methods.

Methods for preparing and using probes and primers are described, for example, in *Molecular Cloning: A Laboratory Manual*, 2nd ed., vol. 1-3, ed. Sambrook et al., Cold Spring Harbor Laboratory Press, Cold Spring Harbor, N.Y., 1989 (hereinafter, "Sambrook et al., 1989"); *Current Protocols in Molecular Biology*, ed. Ausubel et al., Greene Publishing and Wiley-Interscience, N.Y., 1992 (with periodic updates) (hereinafter, "Ausubel et al., 1992"); and Innis et al., *PCR Protocols: A Guide to Methods and Applications*, Academic Press: San Diego, 1990. PCR-primer pairs (a primer set) can be derived from a known sequence, for example, by using computer programs intended for that purpose such as Primer (Version 0.5, @1991, Whitehead Institute for Biomedical Research, Cambridge, Mass.).

Primers and probes based on the flanking genomic DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure and are of sufficient length to maintain this structure under high stringency conditions. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach*, IRL Press, Washington, D.C. (1985), Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a nucleic acid of the present invention will specifically hybridize to one or more of the nucleic acid molecules set forth in SEQ ID NO:5 and SEQ ID NO:6 or complements thereof or fragments of either under moderately stringent conditions, for example at about 2.0× SSC and about 65° C. In a particularly preferred embodiment, a nucleic acid of the present invention will specifically hybridize to one or more of the nucleic acid molecules set forth in SEQ ID NO:5 and SEQ ID NO:6 or complements or fragments of either under high stringency conditions. In one aspect of the present invention, a preferred marker nucleic acid molecule of the present invention has the nucleic acid sequence set forth SEQ ID NO: 5 and SEQ ID NO:6 or complements thereof or fragments of either. In another aspect of the present invention, a preferred marker nucleic acid molecule of the present invention shares between 80% and 100% or 90% and 100% sequence identity with the nucleic acid sequence set forth in SEQ ID NO:5 and SEQ ID NO:6 or complement thereof or fragments of either. In a further aspect of the present invention, a preferred marker nucleic acid molecule of the present invention shares between 95% and 100% sequence identity with the sequence set forth in SEQ ID NO:5 and SEQ ID NO:6 or complement thereof or fragments of either. SEQ ID NO:5 and SEQ ID NO:6 may be used as markers in plant breeding methods to identify the progeny of genetic crosses similar to the methods described for simple sequence repeat DNA marker analysis, in "DNA markers: Protocols, applications, and overviews: (1997) 173-185, Cregan, et al., eds., Wiley-Liss N.Y.; all of which is herein incorporated by reference in its' entirely. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic acid amplification of a target nucleic acid sequence that is part of a nucleic acid template. For example, to determine whether the canola plant resulting from a sexual cross contains transgenic event genomic DNA from the canola plant of the present invention, DNA extracted from a canola plant tissue sample may be subjected to a nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, or plus about fifty nucleotide base pairs, or plus about two hundred-fifty nucleotide base pairs, or plus about three hundred-fifty nucleotide base pairs or more. Alternatively, a primer pair can be derived from flanking genomic sequence on both sides of the inserted DNA so as to produce an amplicon that includes the entire insert nucleotide sequence. A member of a primer pair derived from the plant genomic sequence may be located a distance from the inserted DNA sequence, this distance can range from one nucleotide base pair up to about twenty thousand nucleotide base pairs. The use of the term "amplicon" specifically excludes primer dimers that may be formed in the DNA thermal amplification reaction.

Nucleic acid amplification can be accomplished by any of the various nucleic acid amplification reaction methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or flanking sequence from canola event PV-BNGT04(RT73) can be verified (and corrected if necessary) by amplifying such sequences from the event using primers derived from the sequences provided herein followed by standard DNA sequencing methods applied to the PCR amplicon or to isolated cloned transgene/genomic DNA.

The amplicon produced by these methods may be detected by a plurality of techniques. One such method is Genetic Bit Analysis (Nikiforov, et al. Nucleic Acid Res. 22:4167-4175, 1994) where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal which is measured. A light signal indicates the presence of the transgene insert/flanking sequence due to successful amplification, hybridization, and single or multi-base extension.

Fluorescence Polarization as described by Chen, et al., (Genome Res. 9:492-498, 1999) is a method that can be used to detect the amplicon of the present invention. Using this method an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi, et al. (Nature Biotech. 14:303-308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

DNA detection kits can be developed using the compositions disclosed herein and the methods well known in the art of DNA detection. The kits are useful for the identification of canola event PV-BNGT04(RT73) DNA in a sample and can be applied to methods for breeding canola plants containing PV-BNGT04(RT73) DNA. The kits contain DNA sequences homologous or complementary to SEQ ID NO:7 or SEQ ID NO:8 or to DNA sequences homologous or complementary to DNA contained in the transgene genetic elements of PV-BNGT04(RT73) DNA, these DNA sequences can be used in DNA amplification reactions or as probes in a DNA hybridization method. The sequences of the transgene genetic elements contained in PV-BNGT04(RT73) DNA consists of the Figwort mosaic promoter (U.S. Pat. No. 5,378,619, herein incorporated by reference in its entirety) operably connected to an *Arabidopsis* EPSPS chloroplast transit peptide (At.EPSPS:CTP2, U.S. Pat. No. 5,633,435, herein incorporated by reference in its entirety), operably connected to a glyphosate oxidoreductase gene (U.S. Pat. No. 5,776,760, herein incorporated by reference in its entirety), operably connected to the 3' termination region from pea ribulose 1,5-bisphosphate carboxylase E9 (Coruzzi, et al., EMBO J. 3:1671-1679, 1984, herein incorporated by reference in its entirety), and in tandem orientation, the Figwort mosaic promoter (U.S. Pat. No. 5,378,619) operably connected to an *Arabidopsis* EPSPS chloroplast transit peptide (At.EPSPS:CTP2), operably connected to a glyphosate tolerant 5-enolpyruvylshikimate-3-phosphate synthase (EPSPS) from *Agrobacterium* sp. strain CP4 (AGRTU.aroA:CP4 EPSPS, U.S. Pat. No. 5,633,435, herein incorporated by reference in its entirety), operably connected to the 3' termination region from pea ribulose 1,5-bisphosphate carboxylase E9. DNA molecules useful as primers in DNA amplification methods can be derived from the sequences of the genetic elements of the transgene insert contained in PV-BNGT04(RT73) canola event. These primer molecules can be used as part of a primer set that also includes a DNA primer molecule derived from the genome of PV-BNGT04(RT73) event flanking the transgene insert.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

DNA from PV-BNGT04(RT73) transgenic canola event (hence forth referred to as RT73 event) was extracted from canola seeds containing the RT73 event and nontransgenic canola line Golden Boy. The DNA was isolated from seed tissue using Qiagen's DNeasy Plant Miniprep Kit according to the manufacturer's instructions (Qiagen Corp. Valencia Calif.).

PCR of the genomic sequences flanking the 5' end of the insert in RT73 event was performed using primer 1 sequence (SEQ ID NO: 1, 5' CTTGTTGAGGCTTTGGACTGAGAAT 3') derived from the 5' genomic flanking sequence paired with primer 2 sequence (SEQ ID NO:2, 5' CGCTCTCTCT-TAGTTTTGAAATACA 3') or the complements thereof, located in the insert transgene sequence adjacent to the right border region of the T-DNA. The PCR analysis for the genomic sequence flanking the 3' end of the RT73 event insert was conducted using primer 3 sequence (SEQ ID NO:3, 5' TGAATGTAGACACGTCGAAATAAAGATT 3') located in the transgene sequence coupled with primer 4 (SEQ ID NO:4, 5' TACTTGAAGCACACGACACTGTAATTC 3') or the complements thereof, derived from the 3' genomic flanking sequence. The PCR were performed using ~50 ng of RT73 or nontransgenic genomic DNA template in a 50 µl reaction volume. Each reaction contained 10 mM Tris-HCl, 50 mM KCl, 1.5 mM MgCl$_2$, 200 μM of each DNTP, 0.4 mM each primer, and 2.5 units of RedTaq DNA polymerase. The PCR were performed under the following cycling conditions: 1 cycle at 94° C. for 3 minutes; 35 cycles (or 30 cycles for the 3'-flank analysis) at 94° C. for 30 s, 57.5° C. (or 55° C. for the 3'-flank analysis) for 30 s and 72° C. for 1.5 minutes; 1 cycle at 72° C. for 10 minutes. Twenty microliters of each reaction were separated on a 1.5% agarose gel. The PCR products were visualized by ethidium bromide staining under UV illumination.

PCR products of the expected sizes representing the 5' and 3'transgene/genomic sequences were isolated by separation of the PCR products on a 2.0% agarose gel by electrophoresis. PCR products, representing 5' regions that span the junction between the RT73 event transgenic insertion and the neighboring flanking canola genome DNA sequence were purified by agarose gel electrophoresis followed by isolation from the agarose matrix using the QIAquick Gel Extraction Kit (catalog #28704, Qiagen Inc., Valencia, Calif.). The purified PCR products were then sequenced with by DNA sequence analysis (ABI Prism™ 377, PE Biosystems, Foster City, Calif. and DNASTAR sequence analysis software, DNASTAR Inc., Madison, Wis.).

The DNA sequence was determined for a 353 nucleotide base pair segment representing the 5' transgene/genomic insert sequence of canola RT73 event and identified in SEQ ID NO:7. The DNA sequence was determined for a 474 nucleotide base pair segment representing the 3' transgene/ genomic insert sequence of canola RT73 event and identified in SEQ ID NO:8.

The junction sequences, SEQ ID NO:5 (5'ATCAGTGT-TCGACTTTTT 3') and SEQ ID NO:6 (5' GACATGAAGAT-CATCCTC 3') are novel DNA sequences in RT73 event and are diagnostic for canola plant RT73 event and progeny thereof. The junction sequences in SEQ ID NO:5 and SEQ ID NO:6 represent 9 polynucleotides on each side of an insertion site of the transgene sequence fragment and canola genomic DNA, longer or shorter polynucleotide sequences can be selected from SEQ ID NO:7 or SEQ ID NO:8 that represent the junction sequences. SEQ ID NO:5 is found at nucleotide positions 199-216 of SEQ ID NO:7, and the junction sequence SEQ ID NO:6 is located at nucleotide positions 228-245 of SEQ ID NO:8, representing the transgene/genomic insert junction sequences in RT73 event and progeny thereof.

Example 2

DNA event primer pairs are used to produce an amplicon diagnostic for RT73 event. These event primer pairs include, but are not limited to SEQ ID NO:9 (5' CATGTAGATTTC-CCGGACATGAAG 3') and SEQ ID NO:10 (5'GTGTGAAT-TACAGTGTCGTGTGC 3') or the complements thereof. The amplicon produced by SEQ ID NO:9 and SEQ ID NO: 10 is about 265 polynucleotides. In addition to these primer pairs, any primer pair derived from SEQ ID NO:7 or SEQ ID NO:8 or the complements thereof, that when used in a DNA amplification reaction produces an amplicon diagnostic for RT73 event is an aspect of the present invention. The amplification conditions for this analysis is illustrated in Table 1 and Table 2, however, any modification of these methods that use DNA primers to produce an amplicon diagnostic for RT73 event is within the ordinary skill of the art. In addition, a control primer pair (SEQ ID NO: 11, 5' GTTACAGATGAAGT-TCGGGACG 3' and SEQ ID NO:12, 5' GCAAGAACTG-GCTCTCATTGTG 3') for amplification of an endogenous canola gene (FatA) is included as an internal standard for the reaction conditions and produces an amplicon of approximately 595 polynucleotides. The analysis of RT73 event plant tissue sample should include a positive tissue control from RT73 event, a negative control from a canola plant that is not RT73 event, and a negative control that contains no template canola DNA. Additional primer sequences can be selected from SEQ ID NO:7 and SEQ ID NO:8 by those skilled in the art of DNA amplification methods, and conditions optimized for the production of an amplicon that may differ from the methods shown in Table 1 and Table 2, but result in an amplicon diagnostic for RT73. The use of these DNA primer sequences with modifications to the methods of Table 1 and 2 are within the scope of the invention. The amplicon produced by the use of at least one primer sequence derived from SEQ ID NO:7, or at least one primer sequence derived from SEQ ID NO:8 that when used in a PCR method produces an amplicon diagnostic for RT73 event can be used in the described methods and is an aspect of the invention. The production of the RT73 event amplicon can be performed by using a Stratagene Robocycler, MJ Engine, Perkin-Elmer 9700, or Eppendorf Mastercycler Gradient thermocycler as shown in Table 2, or by methods and apparatus known to those skilled in the art.

TABLE 1

PCR procedure and reaction mixture for the confirmation of RT73 5' transgene insert/genomic junction region.

| Step | Reagent | Amount | Comments |
|---|---|---|---|
| 1 | Nuclease-free water | add to final volume of 20 μl | — |
| 2 | 10X reaction buffer (with MgCl$_2$) | 2.0 μl | 1X final concentration of buffer, 1.5 mM final concentration of MgCl$_2$ |
| 3 | 10 mM solution of dATP, dCTP, dGTP, and dTTP | 0.4 μl | 200 μM final concentration of each dNTP |
| 4 | Event primer 9 (SEQ ID NO: 9 resuspended in 1X TE buffer or | 0.2 μl | 0.1 μM final concentration |

TABLE 1-continued

PCR procedure and reaction mixture for the confirmation of RT73 5' transgene insert/genomic junction region.

| Step | Reagent | Amount | Comments |
|---|---|---|---|
| | nuclease-free water to a concentration of 10 μM) | | |
| 5 | Event primer 10 (SEQ ID NO: 10 resuspended in 1X TE buffer or nuclease-free water to a concentration of 10 μM) | 0.2 μl | 0.1 μM final concentration |
| 6 | Control primer 11 (SEQ ID NO: 11 resuspended in 1X TE buffer or nuclease-free water to a concentration of 10 (μM) | 0.2 μl | 0.1 μM final concentration |
| 7 | Control primer 12 (SEQ ID NO: 12 resuspended in 1X TE buffer or nuclease-free water to a concentration of 10 μM) | 0.2 μl | 0.1 μM final concentration |
| 8 | RNase, DNase free (500 μg/ml) | 0.1 μl | 50 ng/reaction |
| 9 | REDTaq DNA polymerase (1 unit/μl) | 1.0 μl (recommended to switch pipets prior to next step) | 1 unit/reaction |
| 10 | Extracted DNA (template): Samples to be analyzed: | | |
| | individual leaves | 10-200 ng of genomic DNA | |
| | pooled leaves (maximum of 10 leaves/pool) | 200 ng of genomic DNA | |
| | Negative control | 50 ng of non-transgenic canola genomic DNA | |
| | Negative control | no template DNA (solution in which DNA was resuspended) | |
| | Positive control | 50 ng of RT73 genomic DNA | |

Gently mix and, if needed (no hot top on thermocycler), add 1-2 drops of mineral oil on top of each reaction. Proceed with the PCR in a Stratagene Robocycler, MJ Engine, Perkin-Elmer 9700, or Eppendorf Mastercycler Gradient thermocycler using the following cycling parameters (Table 2). The MJ Engine or Eppendorf Mastercycler Gradient thermocycler should be run in the calculated mode. Run the Perkin-Elmer 9700 thermocycler with the ramp speed set at maximum.

TABLE 2

Thermocycler conditions

| Cycle No. | Settings: Stratagene Robocycler |
|---|---|
| 1 | 94° C. 3 minutes |
| 34 | 94° C. 1 minute |
| | 64° C. 1 minute |
| | 72° C. 1 minute and 30 seconds |
| 1 | 72° C. 10 minutes |

| Cycle No. | Settings: MJ Engine or Perkin-Elmer 9700 |
|---|---|
| 1 | 94° C. 3 minutes |
| 34 | 94° C. 30 seconds |
| | 64° C. 30 seconds |
| | 72° C. 1 minute |
| 1 | 72° C. 10 minutes |

| Cycle No. | Settings: Eppendorf Mastercycler Gradient |
|---|---|
| 1 | 94° C. 3 minutes |
| 34 | 94° C. 15 seconds |
| | 64° C. 15 seconds |
| | 72° C. 1 minute |
| 1 | 72° C. 10 minutes |

Example 3 the methods used to identify heterozygous from homozygous canola progeny containing RT73 event DNA are described in the zygosity assay in Table 3 and Table 4. The DNA primers used in the zygosity assay are: SEQ ID NO: 13, 5' CATGTAGATTTCCCGGACATGAAG 3'; SEQ ID NO: 14, 5' GTGTGAATTACAGTGTCGTGTGC 3'; SEQ ID NO: 15, 5' GAGATGTATTTCAAAACTAAGAGAGAGC 3'.

SEQ ID NO:13, SEQ ID NO:14 and SEQ ID NO:15 when used in these reaction methods produce a DNA amplicon of 409 polynucleotide base pairs (bps) for non-transgenic canola, two DNA amplicons of 409 bps and 265 bps for heterozygous canola containing RT73 event DNA, and a DNA amplicon of 265 bp for homozygous canola containing RT73 event DNA. The controls for this analysis should include a positive control from homozygous and heterozygous canola containing RT73 event DNA, a negative control from non-transgenic canola, and a negative control that contains no template DNA. This assay is optimized for use with a Stratagene Robocycler, MJ Engine, Perkin-Elmer 9700, or Eppendorf Mastercycler Gradient thermocycler. Other methods and apparatus known to those skilled in the art that produce amplicons that identify the zygosity of the progeny of crosses made with RT73 event canola plants is within the skill of the art.

TABLE 3

Zygosity assay reaction solutions

| Step | Reagent | Amount | Comments |
|---|---|---|---|
| 1 | Nuclease-free water | add to 20 μl final volume | — |
| 2 | 10X reaction buffer (with $MgCl_2$) | 2 μl | 1.5 mM final concentration of $MgCl_2$ |
| 3 | 10 mM solution of dATP, dCTP, dGTP, and dTTP | 0.4 μl | 200 μM final concentration of each dNTP |
| 4 | SEQ ID NO: 13 primer resuspended in 1X TE buffer or nuclease-free water to a concentration of 10 μM) | 0.5 μl | 0.25 μM final concentration |
| 5 | SEQ ID NO: 14 primer resuspended in 1X TE buffer or nuclease-free water to a concentration of 10 μM) | 0.8 μl | 0.4 μM final concentration |
| 6 | SEQ ID NO: 15 primer resuspended in 1X TE buffer or nuclease-free water to a concentration of 10 μM) | 0.3 μl | 0.15 μM final concentration |
| 7 | REDTaq DNA polymerase (1 unit/μl) | 1.0 μl (recommended to switch pipets prior to next step) | 1 unit/reaction |
| 8 | Extracted DNA (template): Samples to be analyzed (individual leaves) | 10-200 ng of genomic DNA | |
| | Negative control | 10-200 ng of non-transgenic canola genomic DNA | |
| | Negative control | no DNA template (solution in which DNA was resuspended) | |
| | Heterozygous Positive control | 10-200 ng of genomic DNA from known event RT73 heterozygous canola | |
| | Homozygous Positive control | 10-200 ng of genomic DNA from known event RT73 homozygous canola | |

Gently mix and, if needed (no hot top on thermocycler), add 1-2 drops of mineral oil on top of each reaction. Proceed with the PCR in a Stratagene Robocycler, MJ Engine, Perkin-Elmer 9700, or Eppendorf Mastercycler Gradient thermocycler using the following cycling parameters (Table 4). The MJ Engine or Eppendorf Mastercycler Gradient thermocycler should be run in the calculated mode. Run the Perkin-Elmer 9700 thermocycler with the ramp speed set at maximum.

TABLE 4

Zygosity assay thermocycler conditions

| Cycle No. | Settings: Stratagene Robocycler |
|---|---|
| 1 | 94° C. 3 minutes |
| 38 | 94° C. 1 minute |
| | 54° C. 1 minute |
| | 72° C. 1 minute and 30 seconds |
| 1 | 72° C. 10 minutes |

| Cycle No. | Settings: MJ Engine or Perkin-Elmer 9700 |
|---|---|
| 1 | 94° C. 3 minutes |
| 38 | 94° C. 30 seconds |
| | 54° C. 30 seconds |
| | 72° C. 1 minute and 30 seconds |
| 1 | 72° C. 10 minutes |

TABLE 4-continued

Zygosity assay thermocycler conditions

| Cycle No. | Settings: Eppendorf Mastercycler Gradient |
|---|---|
| 1 | 94° C. 3 minutes |
| 38 | 94° C. 15 seconds |
| | 54° C. 15 seconds |
| | 72° C. 1 minute and 30 seconds |
| 1 | 72° C. 10 minutes |

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

We claim:

1. A DNA molecule comprising SEQ ID NO:5.

2. A primer pair of DNA molecules, wherein a first primer of said primer pair comprises at least 11 contiguous nucleotides from nucleotide 208-353 of the transgene region of SEQ ID NO:7 or complements thereof and a second primer of said primer pair comprises at least 11 contiguous nucleotides from nucleotides 1-207 of the canola genomic DNA sequence of SEQ ID NO:7 or complements thereof and the pair of DNA molecules when used together in a DNA amplification method produces a diagnostic amplicon comprising SEQ ID NO:5 or complements thereof for canola event PV-BNGT04(RT73).

3. A method of detecting the presence of genomic/transgene DNA of canola PV-BNGT04(RT73) event comprising SEQ ID NO:5, in a sample, the method comprising:
   (a) contacting the sample comprising canola DNA with a primer pair of claim 2; and
   (b) performing a nucleic acid amplification reaction, thereby producing an amplicon comprising SEQ ID NO:5; and
   (c) detecting the amplicon.

4. The DNA molecule of claim 1, wherein the DNA molecule is SEQ ID NO:7.

5. A DNA detection kit comprising at least one DNA molecule of sufficient length of contiguous nucleotides homologous or complementary to SEQ ID NO:7 to function as a DNA probe specific for canola event PV-BNGT04(RT73), wherein said DNA molecule comprises SEQ ID NO:5.

6. A method of detecting the presence of a genomic/transgene DNA molecule of PV-BNGT04(RT73) comprising SEQ ID NO:5, in a sample, the method comprising:
   (a) contacting the sample comprising canola DNA with a polynucleotide probe that hybridizes under stringent hybridization conditions with DNA from canola event PV-BNGT04(RT73) and does not hybridize under the stringent hybridization conditions with a non-PV-BNGT04(RT73) canola plant DNA, wherein the probe comprises the DNA molecule of claim 1; and
   (b) subjecting the sample and probe to stringent hybridization conditions;
   (c) detecting hybridization of the probe to the DNA.

7. The DNA molecule of claim 1 wherein the DNA molecule is SEQ ID NO:5.

8. A method of selecting a canola plant or seeds thereof comprising a glyphosate tolerant trait, the method comprising the steps of:
(a) obtaining at least one canola plant;
(b) detecting SEQ ID NO:5 within said canola plant; and
(c) selecting a canola plant comprising SEQ ID NO:5.

9. The method of claim 8 further comprising the step of:
(d) producing seed from said canola plant of step (c).

10. A DNA detection kit comprising the primer pair of claim 2.

* * * * *

SEQUENCE LISTING

<160> NUMBER OF SEQ ID NOS: 15

<210> SEQ ID NO 1
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 1
cttgttgagg ctttggactg agaat                                              25

<210> SEQ ID NO 2
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 2
cgctctctct tagttttgaa ataca                                              25

<210> SEQ ID NO 3
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 3
tgaatgtaga cacgtcgaaa taaagatt                                           28

<210> SEQ ID NO 4
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 4
tacttgaagc acacgacact gtaattc                                            27

<210> SEQ ID NO 5
<211> LENGTH: 18
<212> TYPE: DNA
<213> ORGANISM: Artificial sequence
<220> FEATURE:
<223> OTHER INFORMATION: Junction polynucleotides

<400> SEQUENCE: 5
atcagtgttc gactttt                                                       18

<210> SEQ ID NO 6
<211> LENGTH: 18
<212> TYPE: DNA
<213> ORGANISM: Artificial sequence
<220> FEATURE:
<223> OTHER INFORMATION: Junction polynucleotides

<400> SEQUENCE: 6
gacatgaaga tcatcctc                                                      18

<210> SEQ ID NO 7
<211> LENGTH: 353

```
<212> TYPE: DNA
<213> ORGANISM: Artificial sequence
<220> FEATURE:
<223> OTHER INFORMATION: Chimeric DNA of genomic and insert sequence

<400> SEQUENCE: 7
cttgttgagg ctttggactg agaattcttc cttacaaacc tttgaggatg ggagttcctt    60
cttggttttg gcgataccaa tttgaataaa gtgatatggc tcgtaccttg ttgattgaac   120
ccaatctgga atgctgctaa atcctgagct caagcttgat ggggatcaga ttgtcgtttc   180
ccgccttcag tttaaactat cagtgttcga cttttttatgt aacaacccgc cccggatcca  240
accccgaatc cccgtatatt aatagttaag gggtctaaat atagagtgta ttcagatttt   300
atgaattaag gaaatcaatc cttatttacg ctctctctta gttttgaaat aca          353

<210> SEQ ID NO 8
<211> LENGTH: 474
<212> TYPE: DNA
<213> ORGANISM: Artificial sequence
<220> FEATURE:
<223> OTHER INFORMATION: Chimeric DNA of genomic and insert sequence

<400> SEQUENCE: 8
tgaatgtaga cacgtcgaaa taaagatttc cgaattagaa taatttgttt attgctttcg    60
cctataaata cgacggatcg taatttgtcg ttttatcaaa atgtactttc atttttataat  120 aacgctgcgg acatctacat ttttgaattg aaaaaaaatt ggtaattact ctttcttttt   180
ctccatattg accatcatac tcattgctga tccatgtaga tttcccggac atgaagatca   240
tcctccttcc tttccttgcc tttccttcct tttcttgcct tcgtataagc ttgtgtcaat   300
tgttgacaga gaatcttgct gaagaattac tcagaaacag agtacttcaa ggtattgaac   360
attccacatg tggaaatcga cggctagaag taaaaaaaaa aggtaatatt attgtgcata   420
tatataaaaa cataaccccca acgaccttac ttgaagcaca cgacactgta attc         474

<210> SEQ ID NO 9
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 9
catgtagatt tcccggacat gaag                                           24

<210> SEQ ID NO 10
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 10
gtgtgaatta cagtgtcgtg tgc                                            23

<210> SEQ ID NO 11
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 11
```

-continued

```
gttacagatg aagttcggga cg                                        22

<210> SEQ ID NO 12
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 12
gcaagaactg gctctcattg tg                                        22

<210> SEQ ID NO 13
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 13
catgtagatt tcccggacat gaag                                      24

<210> SEQ ID NO 14
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 14
gtgtgaatta cagtgtcgtg tgc                                       23

<210> SEQ ID NO 15
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 15
gagatgtatt tcaaaactaa gagagagc                                  28
```